(12) United States Patent
Bebber

(10) Patent No.: US 8,402,583 B1
(45) Date of Patent: Mar. 26, 2013

(54) MULTIPURPOSE HEALTH CARE PROFESSIONAL TOOL ASSEMBLY

(76) Inventor: Dana M. Bebber, Crofton, MD (US)

(*) Notice: Subject to any disclaimer, the term of this patent is extended or adjusted under 35 U.S.C. 154(b) by 295 days.

(21) Appl. No.: 12/760,046

(22) Filed: Apr. 14, 2010

(51) Int. Cl.
*B25B 7/22* (2006.01)
*B26B 11/00* (2006.01)

(52) U.S. Cl. .................. 7/125; 7/118; 7/135; 362/119; 362/253

(58) Field of Classification Search .............. 362/119, 362/253; 7/135, 118, 125
See application file for complete search history.

(56) References Cited

U.S. PATENT DOCUMENTS

| | | | |
|---|---|---|---|
| 1,200,079 A | 10/1916 | Christensen | |
| 4,149,257 A * | 4/1979 | Nakagiri et al. | 708/111 |
| D362,013 S | 9/1995 | Benjamin | |
| 5,630,664 A | 5/1997 | Farrelly | |
| 5,857,268 A | 1/1999 | Park | |
| 6,167,412 A | 12/2000 | Simons | |
| 6,238,404 B1 | 5/2001 | Hidalgo et al. | |
| 6,273,582 B1 * | 8/2001 | Taggart et al. | 362/119 |
| D463,494 S | 9/2002 | Mori | |
| D551,802 S | 9/2007 | Rubin et al. | |
| 2010/0122419 A1 * | 5/2010 | Zupancic-Albin | 7/125 |

* cited by examiner

*Primary Examiner* — Ahmed Farah
*Assistant Examiner* — William Cheng

(57) ABSTRACT

A multipurpose health care professional tool assembly for providing in one convenient package the specific tools used on a daily basis by health care professionals includes a housing having a top face, a front slot and a rear slot. A calculator is positioned on the top face of the housing. A light is coupled to the housing. A pen is provided having a connection end and a writing end. The connection end is pivotally coupled to the housing in the rear slot such that the pen is extendable from the rear slot of the housing to facilitate writing using the pen. A hemostat tool is pivotally coupled to the housing and extendable from the front slot into a use position.

9 Claims, 5 Drawing Sheets

MULTIPURPOSE HEALTH CARE PROFESSIONAL TOOL ASSEMBLY

BACKGROUND OF THE DISCLOSURE

1. Field of the Disclosure

The disclosure relates to multipurpose tools and more particularly pertains to a new multipurpose tool for providing in one convenient package the specific tools used on a daily basis by health care professionals.

2. Summary of the Disclosure

An embodiment of the disclosure meets the needs presented above by generally comprising a housing having a top face, a front slot and a rear slot. A calculator is positioned on the top face of the housing. A light is coupled to the housing. A pen is provided having a connection end and a writing end. The connection end is pivotally coupled to the housing in the rear slot such that the pen is extendable from the rear slot of the housing to facilitate writing using the pen. A hemostat tool is pivotally coupled to the housing and extendable from the front slot into a use position.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
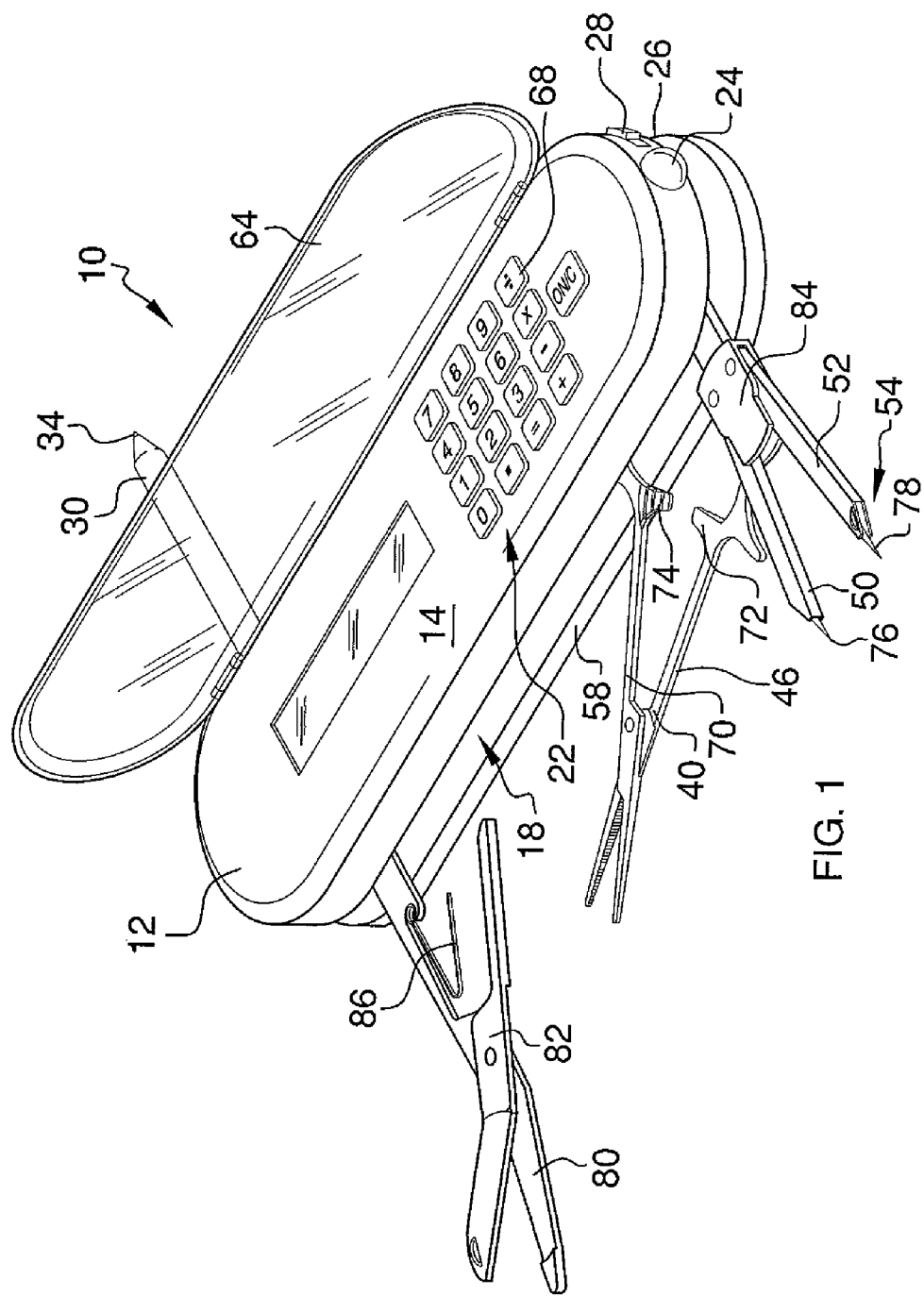
FIG. 1 is a top front side perspective view of a multipurpose health care professional tool assembly according to an embodiment of the disclosure.
Figure 2:
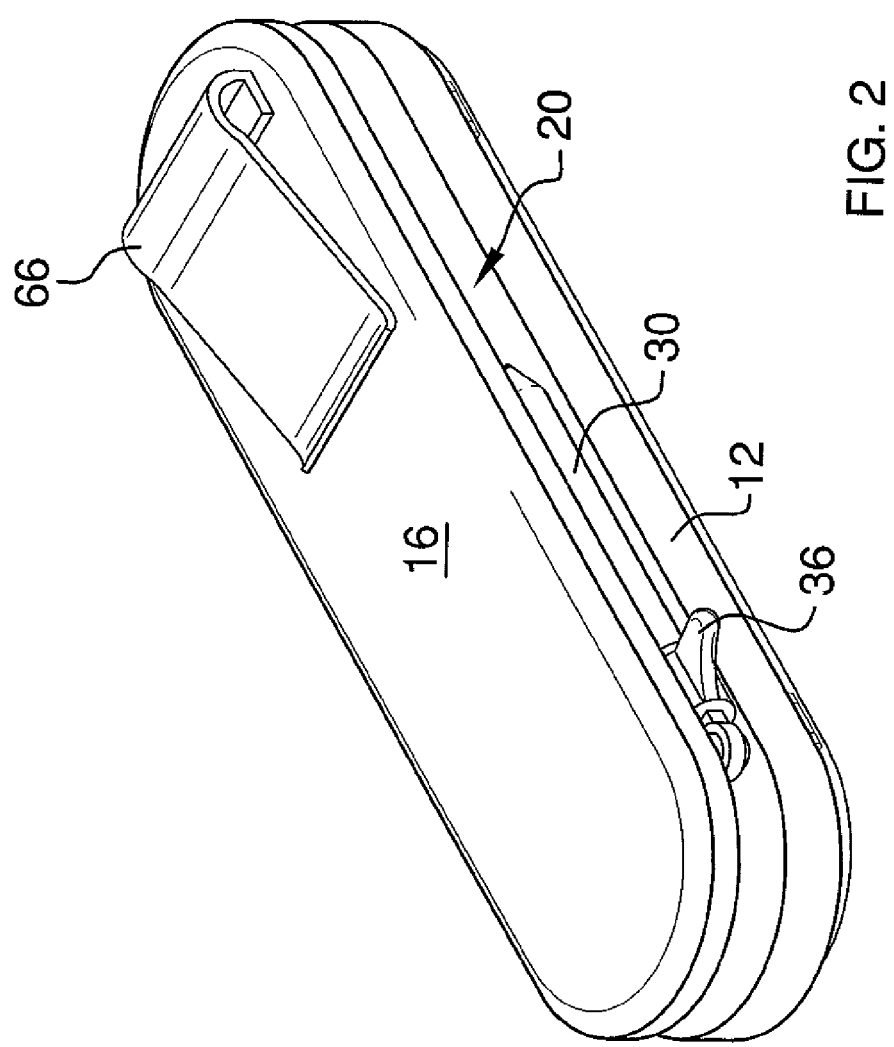
FIG. 2 is a bottom back side perspective view of an embodiment of the disclosure.
Figure 3:
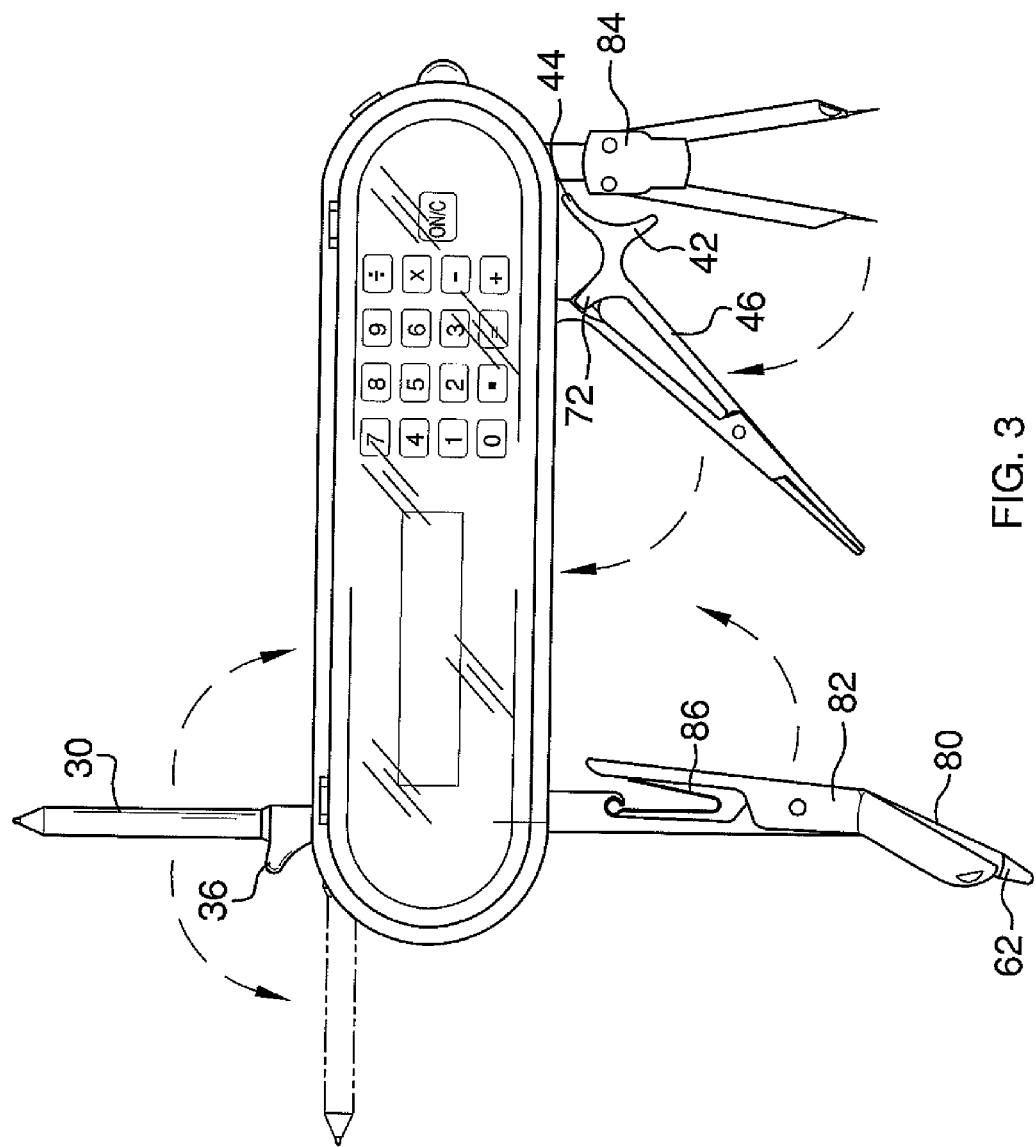
FIG. 3 is a top view of an embodiment of the disclosure.
Figure 4:
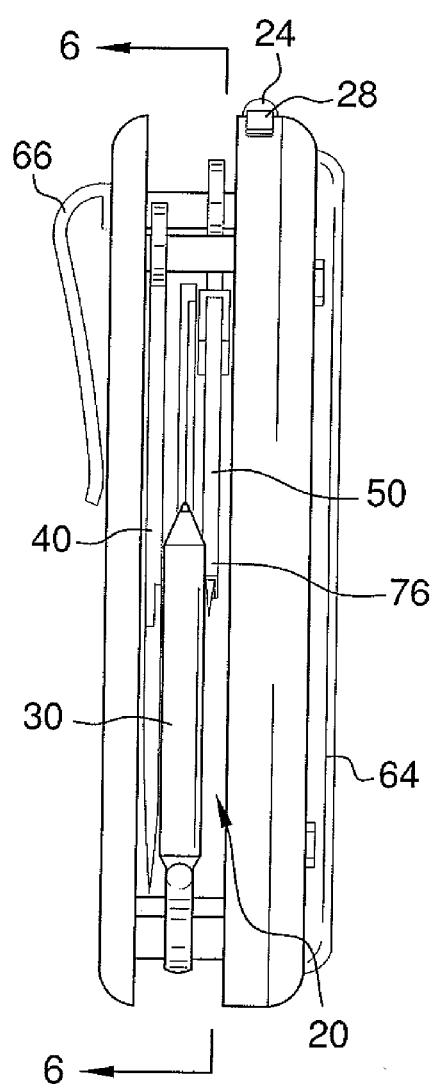
FIG. 4 is a back view of an embodiment of the disclosure.
Figure 5:
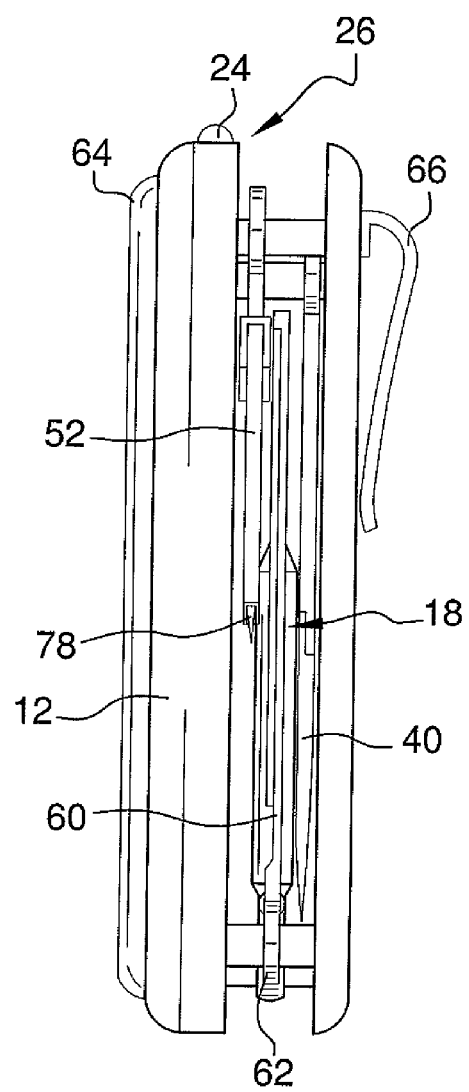
FIG. 5 is a front view of an embodiment of the disclosure.

With reference now to the drawings, and in particular to FIGS. 1 through 6 thereof, a new multipurpose tool embodying the principles and concepts of an embodiment of the disclosure and generally designated by the reference numeral 10 will be described.

As best illustrated in FIGS. 1 through 6, the multipurpose health care professional tool assembly 10 generally comprises a housing 12 having a top face 14, a bottom face 16, a front slot 18 and a rear slot 20. The housing 12 has dimensions of 4 to 5 inches long, 1 to 1.25 inches wide and 0.5 to 0.75 inches thick.

A calculator 22 is positioned on the top face 14 of the housing 12. A light 24 is coupled to the housing 12. The light 24 is positioned at an end 26 of the housing 12. An on/off button 28 is coupled to the housing 12 adjacent to the light 24. The on/off button 28 is operationally coupled to the light 24 for selectively illuminating the light 24.

Figure 6:
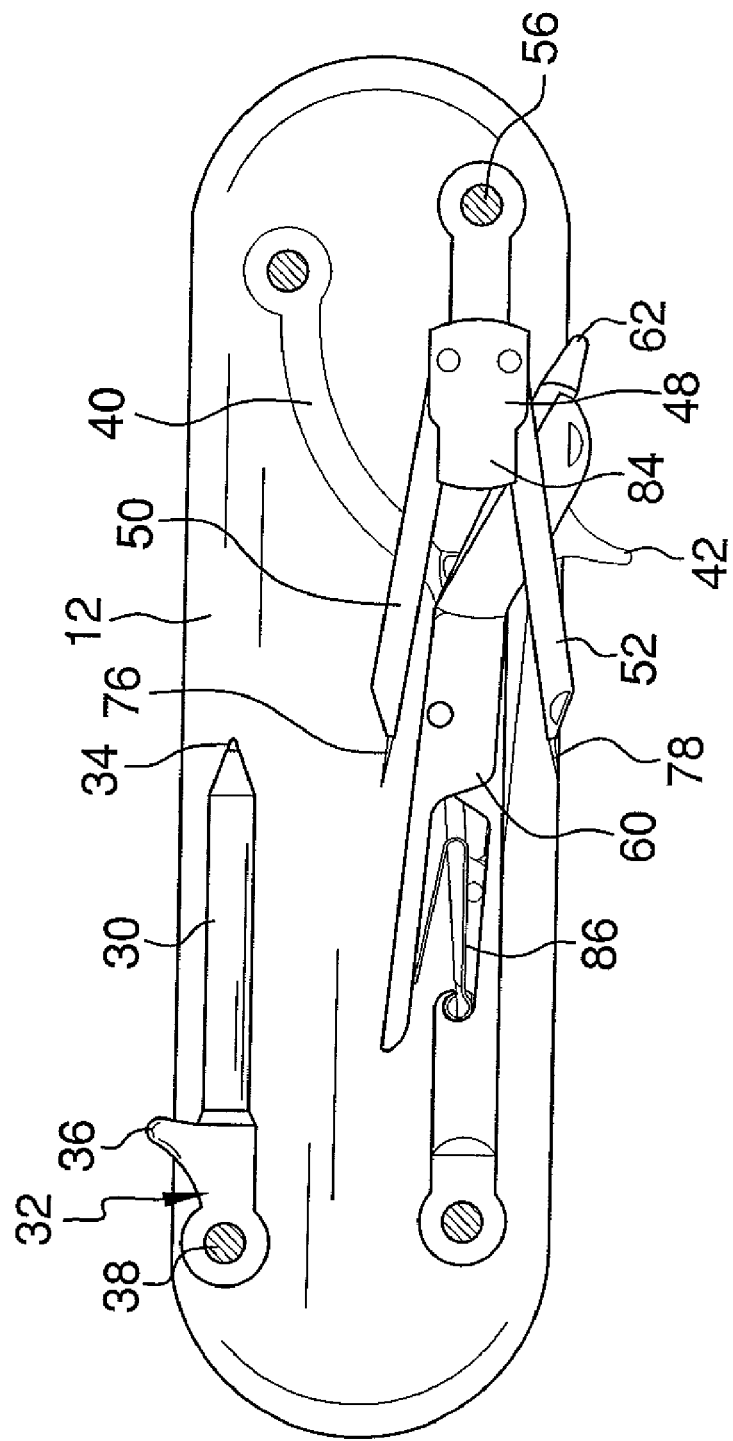
FIG. 6 is a cross-sectional view of an embodiment of the disclosure taken along line 6-6 of FIG. 4.

A pen 30 has a connection end 32 and a writing end 34. The connection end 32 is pivotally coupled to the housing 12 in the rear slot 20 such that the pen 30 is extendable from the rear slot 20 of the housing 12 to facilitate writing using the pen 30. The pen 30 is pivotable into a storage position in the rear slot 20 as shown in FIG. 6. The pen 30 has a protrusion 36 positioned adjacent a pen pivot point 38 such that the protrusion 36 extends from the rear slot 20 when the pen 30 is in the storage position. Preferably, the pen 30 writes in indelible black ink.

A hemostat tool 40 is pivotally coupled to the housing 12. The hemostat tool comprises a pair of medially pivoted arms 46,70. Locking portions 72,74 are provided on each of the arms 46,70 respectively. The hemostat tool 40 is extendable from the front slot 18 into a use position. The hemostat tool 40 has an extension portion 42 positioned proximate an end portion 44 of arm 46 of the hemostat tool 40 such that the extension portion 42 extends from the front slot 18 when the hemostat tool 40 is in a storage position.

A caliper tool 48 has a central portion 84 pivotally coupled to the housing 12. The caliper tool 48 is pivotable into a storage position in the front slot 18 as shown in FIG. 6. The caliper tool 48 has a first arm 50 and a second arm 52 pivotally coupled to the central portion 84. The first arm 50 and the second arm 52 each have a pointed end portion 76,78 respectively. The second arm 52 has a distal end 54 relative to a caliper pivot point 56. The distal end 54 of the second arm 52 is positioned adjacent an outer edge 58 of the front slot 18 for facilitating manipulation of the caliper tool 48 to pivot the caliper tool 48 from the front slot 18.

A bandage scissor tool 60 is pivotally coupled to the housing 12. The bandage scissor tool 60 is pivotable into a storage position in the front slot 18 as shown in FIG. 6. The bandage scissor tool 60 has a tip portion 62 positioned to extend from the front slot 18 when the bandage scissor tool 60 is in the storage position. The bandage scissor tool 60 includes medially pivoted angled arms 80,82 and a biasing member 86 for urging the arms 80,82 open during use.

A cover member 64 is hingedly coupled to the housing 12. The cover member 64 is positioned to cover the top face 14 of the housing 12 when the cover member 64 is in a closed position. A clip member 66 is coupled to the bottom face 16 of the housing 12.

In use, the calculator 22 may be accessed by pivoting the cover member 64 into an open position and selectively pressing buttons 68 as desired. The hemostat tool 40, caliper tool 48, bandage scissor tool 60, and pen 30 may each be pivoted out from storage positions in the front slot 18 or rear slot 20 as desired depending on which tool is needed at a given time.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A multipurpose health care professional tool assembly comprising:
   a housing have a top face, a bottom face, a front slot, and a rear slot;
   a calculator positioned on said top face of said housing, said calculator including a plurality of numerical buttons and arithmetic function buttons configured for performing arithmetic functions, wherein said calculator is configured to be concealed by a cover member hingedly coupled to said housing when said cover member is in a closed position, and wherein said plurality of numerical buttons and arithmetic function buttons on said calculator may be selectively accessed when said cover member is pivoted into an open position;
   a light source coupled to said housing;
   a pen having a connection end and a writing end, said connection end being pivotally coupled to said rear slot of said housing via a pen pivot point, such that said pen is configured to be pivotally rotatable from a storage position where said pen is stored in said rear slot of said housing to a different position configured to facilitate writing use of said pen, wherein when said pen is in said storage position, a protrusion positioned adjacent said pen pivot point extends from said rear slot of said housing; and
   a hemostat tool including a pair of medially pivoted arms and a locking portion provided on each separate medially pivoted arm, said hemostat tool being pivotally coupled to said housing, wherein said hemostat tool is configured to extend from a storage position where said hemostat tool is positioned in a front slot of said housing, and wherein when said hemostat tool is positioned in said storage position, an extension portion of said hemostat tool extends from said front slot.

2. The multipurpose health care professional tool assembly of claim 1, further including a caliper tool pivotally coupled to said housing.

3. The multipurpose health care professional tool assembly of claim 2, wherein said caliper tool is pivotable into a storage position in said front slot.

4. The multipurpose health care professional tool assembly of claim 3, further including said caliper tool having a first arm and a second arm, said second arm having a distal end relative to a caliper pivot point, said distal end of said second arm being positioned adjacent an outer edge of said front slot for facilitating manipulation of said caliper tool to pivot said caliper tool from said front slot.

5. The multipurpose health care professional tool assembly of claim 1, further including a bandage scissor tool pivotally coupled to said housing.

6. The multipurpose health care professional tool assembly of claim 5, wherein said bandage scissor tool is pivotable into a storage position in said front slot.

7. The multipurpose health care professional tool assembly of claim 6, further including said bandage scissor tool having a tip portion positioned to extend from said front slot when said bandage scissor tool is in said storage position.

8. The multipurpose health care professional tool assembly of claim 1, further including a clip member coupled to a bottom face of said housing.

9. A multipurpose health care professional tool assembly comprising:
   a housing have a top face, a bottom face, a front slot, and a rear slot;
   a calculator positioned on said top face of said housing, said calculator including
   a plurality of numerical buttons and arithmetic function buttons configured for performing arithmetic functions, wherein said calculator is configured to be concealed by a cover member hingedly coupled to said housing when said cover member is in a closed position, and wherein said plurality of numerical buttons and arithmetic function buttons on said calculator may be selectively accessed when said cover member is pivoted into an open position;
   a light source coupled to said housing, said light source being positioned at an end of said housing;
   an on/off button coupled to said housing, said on/off button being operationally coupled to said light source for selectively illuminating said light source;
   a pen having a connection end and a writing end, said connection end being pivotally coupled to said rear slot of said housing via a pen pivot point, such that said pen is configured to be pivotally rotatable from a storage position where said pen is stored in said rear slot of said housing to a different position configured to facilitate writing use of said pen, wherein when said pen is in said storage position, a protrusion positioned adjacent said pen pivot point extends from said rear slot of said housing;
   a hemostat tool including a pair of medially pivoted arms and a locking portion provided on each separate medially pivoted arm, said hemostat tool being pivotally coupled to said housing, wherein said hemostat tool is configured to extend from a storage position where said hemostat tool is positioned in a front slot of said housing, and wherein when said hemostat tool is positioned in said storage position, an extension portion of said hemostat tool extends from said front slot;
   a caliper tool pivotally coupled to said housing, said caliper tool being pivotable into a storage position in said front slot;
   said caliper tool having a first arm and a second arm, said second arm having a distal end relative to a caliper pivot point, said distal end of said second arm being positioned adjacent an outer edge of said front slot for facilitating manipulation of said caliper tool to pivot said caliper tool from said front slot;
   a bandage scissor tool pivotally coupled to said housing, said bandage scissor tool being pivotable into a storage position in said front slot;
   said bandage scissor tool having a tip portion positioned to extend from said front slot when said bandage scissor tool is in said storage position;
   and
   a clip member coupled to said bottom face of said housing.

* * * * *